United States Patent
Deneuvillers et al.

(10) Patent No.: US 7,811,307 B2
(45) Date of Patent: Oct. 12, 2010

(54) INTER-LAMINAR SUPPORT

(75) Inventors: Guy Deneuvillers, Merlimont (FR); Piero Petrini, Perugia (IT)

(73) Assignees: Cousin Biotech SAS, Wervicq Sud (FR); Smart Hospital SRL, Lucca (IT)

( * ) Notice: Subject to any disclaimer, the term of this patent is extended or adjusted under 35 U.S.C. 154(b) by 16 days.

(21) Appl. No.: 10/576,935

(22) PCT Filed: Oct. 22, 2004

(86) PCT No.: PCT/FR2004/002727

§ 371 (c)(1), (2), (4) Date: Jun. 20, 2006

(87) PCT Pub. No.: WO2005/044118

PCT Pub. Date: May 19, 2005

(65) Prior Publication Data

US 2007/0112350 A1    May 17, 2007

(30) Foreign Application Priority Data

Oct. 24, 2003   (FR) ................... 03 12487

(51) Int. Cl.
*A61B 17/70*   (2006.01)

(52) U.S. Cl. .................................................. 606/249

(58) Field of Classification Search ............ 606/60–61, 606/246–249; 623/17.11–17.16
See application file for complete search history.

(56) References Cited

U.S. PATENT DOCUMENTS

| | | | | |
|---|---|---|---|---|
| 5,645,599 A | * | 7/1997 | Samani ..................... | 623/17.16 |
| 6,743,257 B2 | * | 6/2004 | Castro ..................... | 623/17.16 |
| 6,761,720 B1 | * | 7/2004 | Senegas ..................... | 606/249 |
| 2001/0016743 A1 | * | 8/2001 | Zucherman et al. ......... | 606/61 |

FOREIGN PATENT DOCUMENTS

| | | | |
|---|---|---|---|
| FR | 2 717 675 A | | 9/1995 |
| JP | 09 075381 A | | 3/1997 |
| WO | WO0128442 | * | 4/2001 |
| WO | WO 2004/084743 A1 | | 10/2004 |

OTHER PUBLICATIONS

Patent Abstracts of Japan, vol. 2003, No. 07, Jul. 3, 2003 & JP 2003 079649 A, Pentax Corp; Hase Hitoshi, Mar. 18, 2003.

* cited by examiner

*Primary Examiner*—Eduardo C Robert
*Assistant Examiner*—Elana B Fisher
(74) *Attorney, Agent, or Firm*—Kenyon & Kenyon LLP

(57) ABSTRACT

A vertebral support for positioning between the laminae of the vertebrae. The support may comprise an anterior portion inserted between the laminae of the vertebrae, suitable for giving an anatomical intervertebral spacing, and a posterior portion providing mobility in the region fitted with the implant. A retaining member may limit displacement of the support by shoulders projecting from the anterior portion of the support, and by two transverse projections.

25 Claims, 4 Drawing Sheets

INTER-LAMINAR SUPPORT

This is a 371 national phase application of PCT/FR2004/002727 filed 22 Oct. 2004, claiming priority to French Patent Application No. FR 0312487 filed 24 Oct. 2003, the contents of which are incorporated herein by reference.

The present invention relates to the technical field of vertebral prostheses for acting between two adjacent vertebrae to redistribute the overloading created by degeneration of the disk, without preventing articular movements from taking place, and leaving the possibility of following the movements of the spine.

BACKGROUND OF THE INVENTION

Prostheses comprising a portion made of deformable material are already known. In French patent No. 2 623 085 in the name of Francis Breard, there is described a kind of spacer having two ends and suitable for being inserted between the spinous processes of two adjacent vertebrae. The spacer is held by means of ligaments passing through lateral holes.

A prosthesis of a very similar design is described in European patent No. 0 322 334 to inventor Jean-Jacques Bronsard. One or more hollow resilient cylindrical pads are described therein as being interposed between the spinous processes of two adjacent vertebrae, and as being secured by means of a ligament passing through the pads. Other inter-process prostheses of a variety of shapes are described in French patents Nos. 2 717 675 and 2 775 183 to Dr. Jean Taylor.

Although those known devices provide results that are advantageous in terms of disk spacing, by being secured between spinous processes, they nevertheless suffer from drawbacks that are not negligible since they do not provide any means for recovering the ability to support loads that are appropriate to physiological requirements. The absorption of load transmission between vertebrae has until now remained partial only.

Since such prostheses interposed between the spinous processes are off-center relative to the center of gravity of the vertebrae bodies, which carry the maximum load, whereas the major fraction of the load passes via an axis situated in the centers of the vertebral bodies.

The first disadvantage of such prior devices is that only a portion of the load is absorbed by the prosthesis, thus preventing it from having a damping function that is fully effective.

The second disadvantage is that the articular mobility of prostheses of that type is small, with full control over flexing, extension, and rotation of the spine then being substantially limited.

The third disadvantage is that those known devices are all invasive since it is necessary to remove the healthy posterior ligament or to damage the adjacent lateral muscles in order to put them in place.

OBJECTS AND SUMMARY OF THE INVENTION

The vertebral implant of the present invention remedies such drawbacks by means of its materials, its functional aspect, and its shapes specifically adapted to providing effective damping as close to possible to the vertebral canal. The presence of flexible resilient bodies for insertion between two adjacent vertebrae in the space between the under- and overlying laminae beside the region fitted with the implant, stabilizes the support in an anterior/posterior direction by using integral retaining means.

One of the numerous advantages of the inter-laminar support is to bring the support point to the posterior arc, i.e.., to the place where the load is at its greatest.

The bearing point of the functional unit, on which the load absorbed by the spine is concentrated while it is in movement, is positioned gradually towards the posterior portion of the medulary canal and is situated exactly in the inter-laminar portion away from the articular portions of the vertebrae, as close as possible to the medulary center for distributing the forces accommodated during movements of the spinal column.

The distance between the axis of said resilient body and the center of gravity of the vertebral body is then considerably reduced, compared with the above-described prior art devices.

Another advantageous function of this inter-laminar implant is to restore and maintain a satisfactory disk spacing and to provide better damping of the forces acting at this level, providing better relief for the intervertebral disk.

The constituent materials and the shapes of the inter-laminar support enable it to be put into place between the laminae of the vertebrae of the posterior portion of the vertebral column, and most particularly in the dorso-lumbar, and lumbo-sacral regions, with its shape adapting to the anatomical variations in the regions concerned.

The pliability and the flexibility of the materials from which the intervertebral support is made makes it possible to retain a hinge point allowing for three-dimensional mobility, while providing an anatomical intervertebral space that is stable.

Its compact size makes it possible to reduce the amount of healthy ligament and muscle holding the articular portions that needs to be removed. While the implant is being put into place, the preparation space is restricted to a minimum that can accept the thrust from the implant between the laminae in the region fitted with the implant, while leaving a maximum amount of tissue intact. The implant is micro-invasive.

The invention consists in an intervertebral support enabling an anatomical intervertebral space to be maintained and restoring three-dimensional mobility to the region fitted with the implant, and it comprises a spacer with retaining means. The invention comprises two portions.

A posterior portion provides mobility and damping in the region fitted with the implant. It comprises retaining means serving to prevent the support migrating towards the anterior portion of the spine, by pressing against the laminae. An anterior portion, suitable for being received between the laminae of the vertebrae restores an anatomical intervertebral spacing.

Retaining means, constituted by lateral shoulders, transverse projections on the top and bottom portions of the implant, and grooves molded in the anterior portion, enable the implant to be held in place and kept pressed in abutment at the junction between the laminae and the processes. This makes it possible to prevent the support from migrating towards the anterior portion of the spine.

The lateral shoulders of the posterior portion may be constituted by large symmetrically- opposite areas, set back from the anterior portion and suitable for being received against the laminae of the vertebrae as close as possible to the articular portions. The shoulders may also have small area, being of the type constituted by projecting bulges that are symmetrically opposite and set back from the anterior portion, being suitable for releasing movement of the vertebral articular portions.

The height of the lateral shoulders does not exceed the greatest height of the posterior portion of the support and they are narrow in width compared with the support taken as a whole.

The posterior portion includes a bottom portion that is carried on the top portion of the underlying process.

In a variant design, this posterior portion serving to damp movements between two adjacent vertebrae is made to have a prismatic shape of height corresponding to the spacing between the adjacent vertebrae, with at least one corner thereof being rounded, the top portion of the posterior portion of the spacer being triangular in shape, so as to receive the tip of the junction formed by the laminar and the process. This shape gives stability between the vertebrae over- and underlying said region fitted with the implant.

In another design, the posterior portion provides freedom of movement between the top portion of the spacer and the process above the region fitted with the implant, because of the tapering shape of the posterior portion.

The posterior portion of the device presents top and bottom surfaces that are flared in their anterior portions, going as far as the transverse projections, and tapering progressively towards the extreme posterior portions of said surfaces, and receiving the junction point formed by the laminar at the process.

The core of the posterior portion can be pierced by a through recess enabling the flexibility of the assembly to be increased.

The core of the posterior portion may support teeth that are spaced apart by furrows, the teeth being opposite in pairs, on the bottom and top portions, enabling the flexibility of the assembly to be varied.

The vertical portions of the shoulders in contact with the laminae present portions that are sufficiently concave and tapering towards the posterior lateral portion of the device to release space for the articular portions.

The material enabling the modulus of elasticity to be defined is silicone, having hardness in the range 40 to 80 on the Shore A scale. It enables the modulus of elasticity to be defined that is adapted to the stresses that arise while nevertheless serving, at least in part, to allow freedom of movement to the region fitted with the implant. At least the posterior portion thereof is made of silicone.

In a variant design, the invention has additional retaining means constituted by ligaments, and where appropriate by holes extending vertically through the implant to pass the ligaments. These ligaments may be independent or crossed and they pass through the support over its entire length or width. Holes are provided for them to pass through.

The support may be coated in part with a biocompatible knit fabric while leaving the anterior portion bare to avoid fibrosis beside healthy tissue.

The anterior portion of the support includes in its core a loop of rigid biocompatible material. In a variant design, the anterior portion is constituted entirely out of rigid biocompatible material.

In its middle and extending lengthwise, the posterior portion presents a shallow groove suitable for coming into contact with the process above the region fitted with the implant.

BRIEF DESCRIPTION OF THE DRAWINGS

The accompanying drawings given by way of non-limiting indication are described in greater detail.

DETAILED DESCRIPTION

In an embodiment, the support is made of silicone having hardness lying in the range 40 to 80 on the Shore A scale, or it is made of polyethylene at the support portions for the laminae.

The support is made of biocompatible material, allowing a certain amount of movement along all axes, so as to adapt to the complex movements of the vertebrae. Silicone can vary the damping effect of the implant. Such a support can be obtained by injection molding silicone of a medical grade that is implantable at more than thirty days.

In a preferred embodiment, the implant is obtained by overmolding silicone around a loop (12) of polyetheretherketone or of biocompatible metal that is disposed in the center of the anterior portion (1).

Ideally, the support is incorporated and self-supporting between the medulary center and the articular axis of the spinal column, as close as possible to the medulary canal but without being in contact with the dura mater. The anterior portion (1) of the support remains as bare silicone so as to avoid fibrosis, thus enabling the implant to be located close to the dura mater. The remainder of the support or implant is covered in a biocompatible knit fabric.

Figure 1:
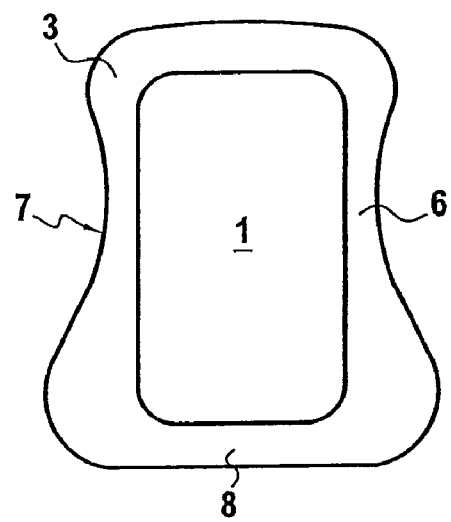
FIG. 1 is an end view of the anterior face of the invention.
Figure 2:
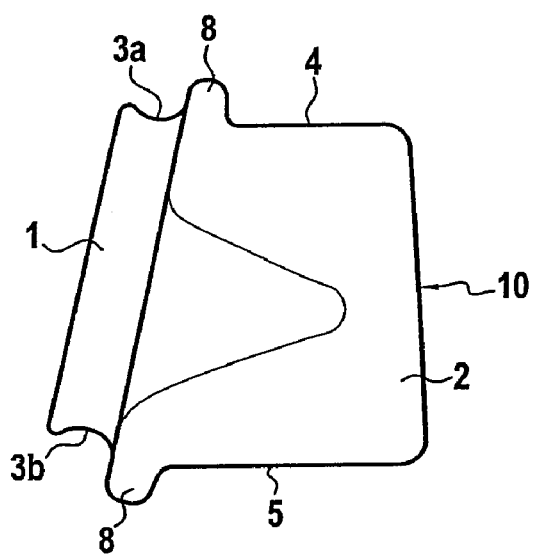
FIG. 2 is a side view.
Figure 3:
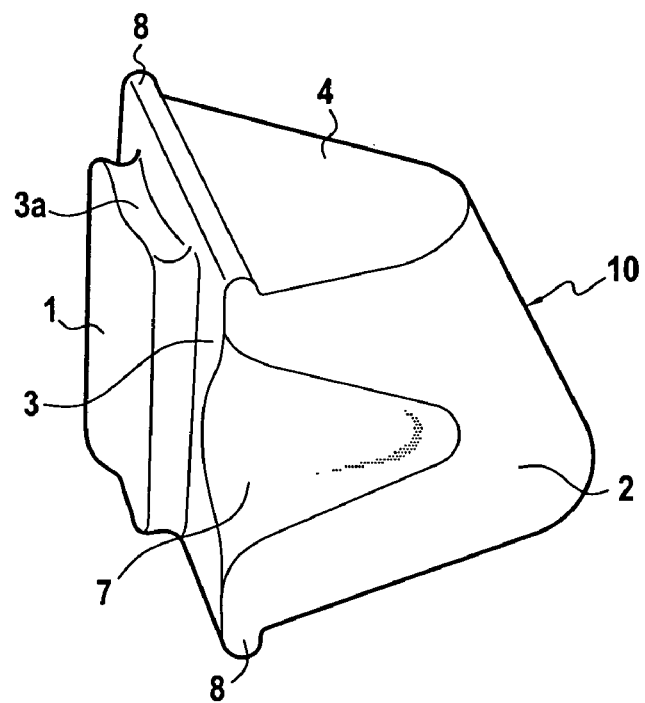
FIG. 3 is a perspective view.
Figure 4:
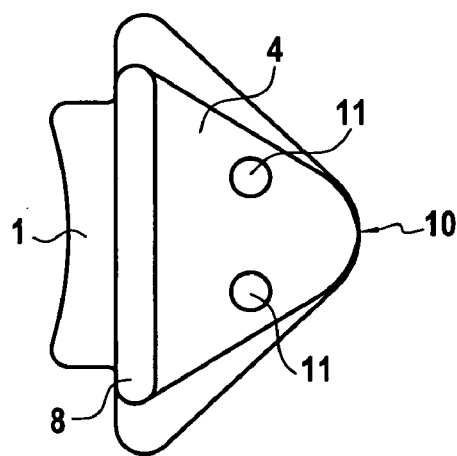
FIG. 4 is a plan view in which the implant presents passages for ligaments.
Figure 5:
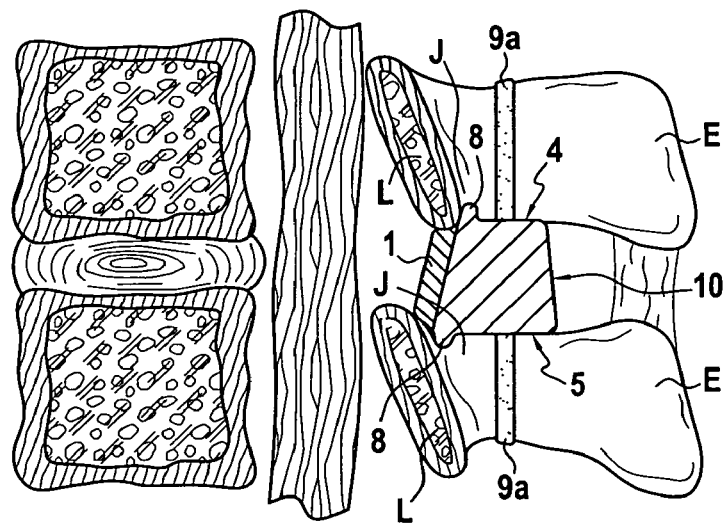
FIG. 5 is a view of the implant in accordance with the invention, provided with ligaments, after being put into place between two vertebrae.
Figure 6:
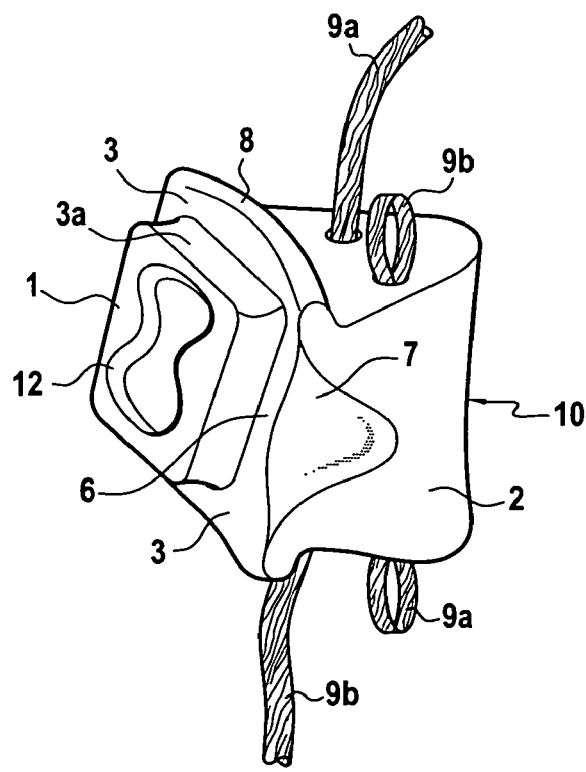
FIG. 6 is a perspective view.
Figure 7:
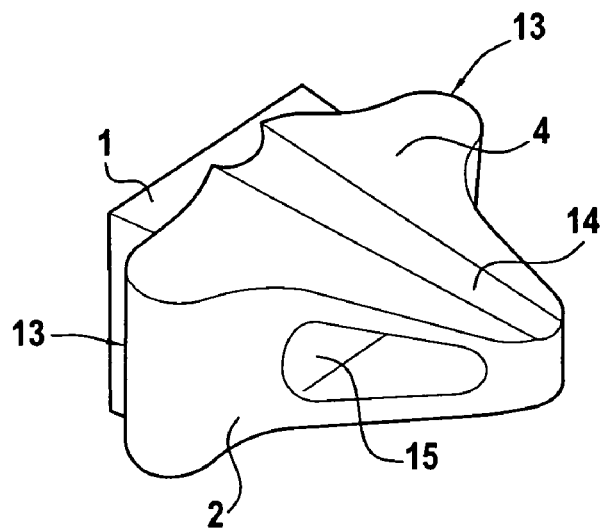
FIG. 7 is a perspective view.
Figure 8:
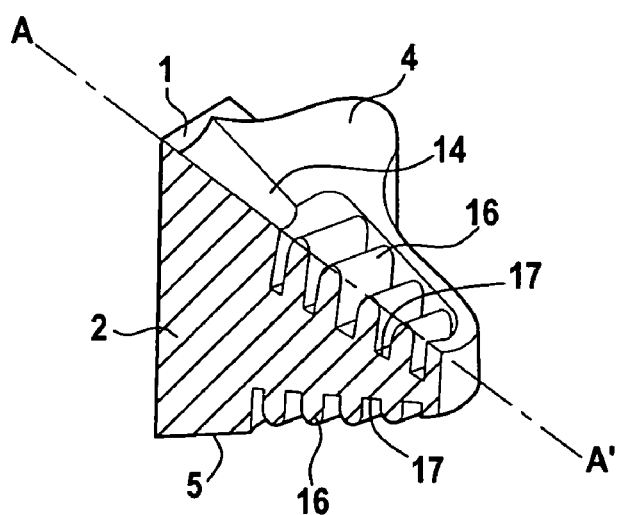
FIG. 8 is a perspective view in section on plane

In a particular embodiment, the posterior portion (2) of the support is prismatic and comprises a support surface (3) in abutment against the laminae (L) projecting from the anterior portion (1) so as to avoid any possibility of the anterior portion (1) moving towards the medulary canal. Also, as shown in FIG. 2, the anterior (1) can project outwardly from the support surface (3) to form a ridge (1a).

The top portion (4) of the posterior portion of the spacer is flared so as to receive the junction point (J) formed by the laminar (L) and the process (E). The bottom portion (5) bears against the top portion of the underlying process (E).

The edge (10) of the posterior portion (2) presents a rounded angle. The vertical portion (6) of the bearing surfaces (3) presents a portion (7) that is sufficiently concave to release the space of the articular portions.

The retaining means, adapted to the inter-laminar space and enabling optimum adaptation of the implant comprise two transverse projections (8) molded in the silicone body, one on the top portion (4) of the implant and the other on the bottom portion (5) of the implant, together with two grooves (3a and 3b) in the anterior portion (1). In alternative embodiments, the retaining means, or lateral shoulders, are broad symmetrically-opposite surfaces (13) set back from the anterior portion.

The implant can thus be positioned without using a ligament at the junction (J) between the laminae and the processes. The surgeon should initially make two notches in the processes in order to receive the projections and thus prevent the support from moving rearwards.

In a variant design, the core of the posterior portion 2) is pierced by a through recess (15), enabling the assembly to be made more flexible.

In another variant design, the core of the posterior portion supports teeth (16) spaced apart by furrows (17) that are opposite in pairs on the top and bottom surfaces and that enable the flexibility of the assembly to be varied.

In a variant design, crossed ligaments (9a, 9b) pass through the middle of the support, holes (11) being provided in its vertical direction. The first ligament is secured to the loop of the second ligament, situated at the base of the support, and vice versa. Each of them goes round one of the processes above or below the level containing the implant.

Another variant design consists in a shallow groove (14) being molded lengthwise in the middle of the top portion (4) of the posterior portion (2).

Naturally, numerous variants could be implemented, in particular by substituting analogous means, without thereby going beyond the ambit of the invention.

The invention claimed is:

1. An intervertebral support for restoring and maintaining an anatomical intervertebral spacing and for restoring three-dimensional mobility where the support is installed, the support comprising:
    an anterior portion and a posterior portion,
    wherein the anterior portion has a planar face, and upper and lower faces configured to respectively receive underlying and overlying laminae of two adjacent vertebrae for restoring an anatomical intervertebral spacing,
    wherein the posterior portion comprising a support surface configured to abut against the laminae, and the support surface having at least a height greater than a height of the planar face so as to form a retaining member for preventing the support from migrating towards the anterior portion of the spine by pressing against the laminae,
    wherein the anterior portion extends outwardly from the support surface of the posterior portion so that upper and lower ridges are formed between the planar face of the anterior portion and the support surface of the posterior portion,
    wherein the upper and lower faces are located on the upper and lower ridges, and
    wherein the posterior portion tapers from the support surface in a direction opposite to the anterior portion and towards a posterior end of the support.

2. A support according to claim 1, wherein the upper and lower faces form grooves.

3. A support according to claim 1, wherein the posterior portion serves to damp movements between two adjacent vertebrae.

4. A support according to claim 1, wherein a bottom face of the posterior portion bears on a top portion of a process at a bottom of a space fitted with the support.

5. A support according to claim 1, wherein the posterior portion is prismatic in shape and of a height that-corresponds to a spacing between the adjacent vertebrae, presenting at least one rounded corner, a top face of the posterior portion being triangular in shape, so as to receive the junction point formed by the lamina and processes.

6. A support according to claim 1, wherein the posterior portion permits a freedom of movement between the a top face of the support and laminae located above a region fitted with the support.

7. A support according to claim 1, wherein the posterior portion presents a top surface and a bottom surface that are flared to the anterior end of the support, tapering progressively towards posterior ends of said surfaces, and receiving the junction point formed by the lamina and the process.

8. A support according to claim 1, wherein a core of the posterior portion is pierced by a through recess, enabling flexibility of the support to be increased.

9. A support according to claim 1, wherein at least the posterior portion is made of silicone having hardness lying in the range 40 to 80 on the Shore A scale, allowing freedom of movement in a region fitted with the support, and flexibility in order to relieve lordosis.

10. A support according to claim 1, wherein a biocompatible knit fabric covers at least part of the posterior portion of the support.

11. A support according to claim 1, wherein the anterior portion of the support has a loop of rigid biocompatible material in its center.

12. A support according to claim 1, wherein the anterior portion of the support is constituted entirely out of rigid biocompatible material.

13. A support according to claim 1, including additional retention means constituted by ligaments crossing in a center of the support, and holes extending vertically for passing the ligaments.

14. A support according to claim 1, including additional retaining means constituted by independent ligaments passing through a full height of the support.

15. An intervertebral support for restoring and maintaining an anatomical intervertebral spacing and for restoring three-dimensional mobility where the support is installed, the support comprising:
    an anterior portion and a posterior portion,
    wherein the anterior portion has a planar face, and upper and lower faces configured to respectively receive the underlying and overlying laminae of two adjacent vertebrae for restoring an anatomical intervertebral spacing,
    wherein the posterior portion comprising a support surface configured to abut against the laminae, and the support surface having at least a height greater than a height of the planar face so as to form a retaining member for preventing the support from migrating towards the anterior portion of the spine by pressing against the laminae,
    wherein the retaining member includes lateral shoulders set back from the anterior portion suitable for being received against the laminae of the vertebrae as close as possible to the articular facets,
    wherein the anterior portion extends outwardly from the support surface of the posterior portion so that the upper and lower ridges are formed between the planar face of the anterior portion and the support surface of the posterior portion, and
    wherein the upper and lower faces are located on the upper and lower ridges.

16. A support according to claim 15, wherein the lateral shoulders are of small area being of the type having symmetrically-opposite projecting bulges set back from the anterior portion and suitable for releasing movement of the vertebral articular facets.

17. A support according to claim 15, wherein the upper and lower faces form grooves, and wherein the lateral shoulders present height that does not exceed a height of the posterior portion of the support, and are narrow in width.

18. A support according to claim 15, wherein the posterior portion presents a top surface and a bottom surface that are flared to the anterior end of the support, tapering progressively towards posterior ends of said surfaces, and receiving a junction point formed by the lamina and the process.

19. A support according to claim 15, wherein a core of the posterior portion is pierced by a through recess, enabling flexibility of the support to be increased.

20. A support according to claim 15, wherein a core of the posterior portion carries teeth spaced apart by furrows, and opposed to each other in pairs on bottom and top faces of the posterior portion, enabling the flexibility of the assembly to be varied.

21. A support according to claim 15, wherein at least the posterior portion is made of silicone having hardness lying in the range 40 to 80 on the Shore A scale, allowing freedom of movement in a region fitted with the support, and flexibility in order to relieve lordosis.

22. A support according to claim 15, wherein a top face of the posterior portion presents a shallow groove extending lengthwise in its middle and suitable for coming into contact with a process above the region fitted with the implant.

23. A method for restoring and maintaining anatomical intervertebral spacing, and for restoring three-dimensional mobility where an intervertebral support is installed, the method comprising:

providing an intervertebral support including anterior and posterior portions, wherein the anterior portion has a planar face, and upper and lower faces configured to respectively receive underlying and overlying laminae of two adjacent vertebrae for restoring an anatomical intervertebral spacing, wherein the posterior portion comprises a support surface configured to abut against the laminae, and the support surface having at least a height greater than a height of the planar face so as to form a retaining member for preventing the support from migrating towards the anterior portion of the spine by pressing against the laminae, wherein the anterior portion extends outwardly from the support surface of the posterior portion so that upper and lower ridges are formed between the planar face of the anterior portion and the support surface of the posterior portion, wherein the upper and lower faces are located on the upper and lower ridges, and wherein the posterior portion tapers from the support surface in a direction opposite to the anterior portion and towards a posterior end of the support, positioning the anterior portion of the intervertebral support in a space between the underlying and overlying laminae of two adjacent vertebrae for restoring an anatomical intervertebral spacing, and arranging the retaining member of the posterior portion of the intervertebral support so that it presses against the laminae to prevent the intervertebral support from migrating towards the anterior portion of the spine and for restoring three-dimensional mobility.

24. The method of claim 23, wherein the retaining member includes two transverse projections, one of which extends from a top face of the posterior portion, and the other of which extends from a bottom face of the posterior portion.

25. The method of claim 23, wherein the retaining member includes lateral shoulders set back from the anterior portion suitable for being received against the laminae of the vertebrae as close as possible to the articular facets.

\* \* \* \* \*